(12) United States Patent
Ikeno et al.

(10) Patent No.: US 6,509,488 B2
(45) Date of Patent: Jan. 21, 2003

(54) METHOD FOR PURIFYING FLUOROARYL METAL COMPOUND

(75) Inventors: Ikuyo Ikeno, Osaka (JP); Hitoshi Mitsui, Kitakatsuragi (JP); Toshiya Iida, Suita (JP); Toshimitsu Moriguchi, Takatsuki (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/993,891

(22) Filed: Nov. 27, 2001

(65) Prior Publication Data

US 2002/0065425 A1 May 30, 2002

(30) Foreign Application Priority Data

Nov. 29, 2000 (JP) ........................................ 2000-367745

(51) Int. Cl.$^7$ .................................................. C07F 7/22
(52) U.S. Cl. .......................................... 556/95; 556/96
(58) Field of Search ...................... 556/95, 96

(56) References Cited

U.S. PATENT DOCUMENTS 3,392,178 A * 7/1968 Tamborski ................... 556/95

FOREIGN PATENT DOCUMENTS

WO  WO 00/17208  3/2000

OTHER PUBLICATIONS

"Polyfluoroaryl Organometallic Compounds Part I.[1] Pentafluorophenyl Derivatives of Tin." (R.D.Chambers, et al., J. Chem. Soc., Jan. 24$^{th}$ 1964, pp. 4782–4790.
Synthesis, Properties, and Hydroboration Activity of the Highly Electrophilic Borane Bis (pentafluorophenyl) borane, HB $(C_6F_5)_2$,[1] (Daniel J. Parks et al., Organometallics, Aug. 5, 1998, pp. 5492–5503).

* cited by examiner

Primary Examiner—Porfirio Nazario-Gonzalez
(74) Attorney, Agent, or Firm—Nixon & Vanderhye, P.C.; Frank P. Presta

(57) ABSTRACT

In a method for purifying a fluoroaryl metal compound of the present invention, magnesium halide is precipitated and removed from a solution containing the fluoroaryl metal compound, the magnesium halide, and an ether solvent. Or, the magnesium halide is removed by treating the solution with an acid. Examples of the method include: a method in which a solvent which has a boiling point higher than that of the ether solvent contained in the solution and which does not dissolve the magnesium halide is heated to a temperature higher than the boiling point of the ether solvent, then the ether solvent is distilled out with the solution being added to the solvent; and a method in which the solution and an aqueous solution containing an acid are mixed and stirred, then allowed to stand so as to be separated into an organic layer containing the fluoroaryl metal compound and an aqueous layer containing the magnesium halide and the acid. In this manner, a highly pure fluoroaryl metal compound having no impurities can be purified easily and inexpensively.

23 Claims, No Drawings

METHOD FOR PURIFYING FLUOROARYL METAL COMPOUND

FIELD OF THE INVENTION

The present invention relates to a method for purifying a fluoroaryl metal compound such as bis(pentafluorophenyl) dimethyltin or bis(pentafluorophenyl)dibutyltin, which is useful, for example, as a pharmaceutical and agricultural chemical intermediate, a polymerization catalyst, a polymerization co-catalyst, a catalyst for photopolymerization of silicone, and intermediates of these catalysts.

BACKGROUND OF THE INVENTION

A fluoroaryl metal compound such as bis(pentafluorophenyl)dimethyltin or bis(pentafluorophenyl) dibutyltin is a useful compound, for example, as a pharmaceutical and agricultural chemical intermediate, a polymerization catalyst, a polymerization co-catalyst, a catalyst for photopolymerization of silicone, and intermediates of these catalysts.

For example, J. Chem. Soc., (1964) 4782 discloses a method for reacting pentafluorophenyl magnesium bromide, obtained by reacting bromopentafluorobenzene with magnesium by means of the Grignard reaction using diethyl ether as a solvent, with dimethyltin dibromide over two days at a reflux temperature, and for synthesizing bis(pentafluorophenyl)dimethyltin in a yield of 58 percent. In the foregoing production method, since diethyl ether, which is a compound having a low boiling point, is used as the solvent, it is difficult to control the temperature of a reaction system, and special caution is required in handling diethyl ether as it is highly flammable.

Besides, for example, Organometallics., (1998) 5492 discloses a method for reacting pentafluorophenyllithium, obtained by reacting bromopentafluorobenzene with butyllithium at −78° C. using diethyl ether as a solvent, with dimethyltin dichloride at −78 C., and for synthesizing bis(pentafluorophenyl)dimethyltin in a yield of 95 percent. However, in the foregoing production method, it is required to cool down a reaction system to −78° C., which is difficult to carry out industrially.

In the production method described in J. Chem. Soc., (1964) 4782, the reaction of pentafluorophenyl magnesium bromide and dimethyltin dibromide produces not only the bis(pentafluorophenyl)dimethyltin, which is an object, but also magnesium dibromide, which is magnesium halide, as a by-product. Since magnesium dibromide is soluble in a solvent such as diethyl ether, in order to purify the bis(pentafluorophenyl)dimethyltin, it is necessary to remove the magnesium dibromide from a solution.

For example, J. Chem. Soc., (1964) 4782 and WO 00/17208 (published on Mar. 30, 2000) disclose a method for removing magnesium halide by treating a reaction solution containing the magnesium halide with an aqueous ammonium chloride solution.

However, when the reaction solution is treated with the aqueous ammonium chloride solution, it becomes difficult to separate an organic layer and an aqueous layer. Therefore, it is hard to say that purifying the bis(pentafluorophenyl) dimethyltin obtained, for example, by the production method described in J. Chem. Soc., (1964) 4782, by means of, for example, the purifying method described in J. Chem. Soc., (1964) 4782 and WO 00/17208 is industrially advantageous. Incidentally, when a fluoroaryl metal compound containing magnesium halide as an impurity is used, for example, as a polymerization catalyst, the activity of the catalyst is significantly decreased.

Consequently, a method for easily and inexpensively purifying a fluoroaryl metal compound produced by various producing methods has been desired.

SUMMARY OF THE INVENTION

It is therefore an object of the present invention to provide a method for purifying a fluoroaryl metal compound easily and inexpensively, so as to obtain a highly pure fluoroaryl metal compound having no impurities.

In order to attain the foregoing object, a method for purifying a fluoroaryl metal compound of the present invention, which is represented by General Formula (1):

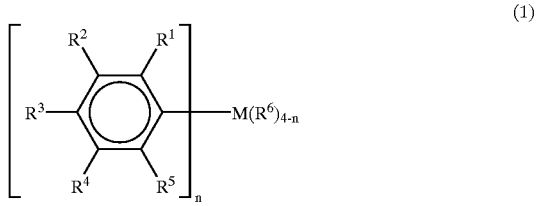

where each of $R^1$, $R^2$, $R^3$, $R^4$, and $R^5$ independently represents one of a hydrogen atom, a fluorine atom, a hydrocarbon group, and an alkoxy group, provided that at least one of $R^1$–$R^5$ represents a fluorine atom, M represents a metal atom which belongs to the group IV, $R^6$ represents a hydrocarbon group, and n represents one of 1 through 3, is characterized by including the step of precipitating and removing magnesium halide represented by General Formula (2):

$$MgX_aX_b \qquad (2)$$

where $X_a$ represents one of a fluorine atom, a chlorine atom, a bromine atom, and an iodine atom, and $X_b$ represents one of a chlorine atom, a bromine atom, and an iodine atom, from a solution containing the fluoroaryl metal compound, the magnesium halide, and an ether solvent.

In other words, to attain the foregoing object, the method for purifying a fluoroaryl metal compound of the present invention, which is represented by General Formula (1), is characterized by including the step of removing magnesium halide, which is represented by General Formula (2), from a solution containing the fluoroaryl metal compound, the magnesium halide, and an ether solvent, by treating the solution with an acid.

Further objects, features, and advantages of the present invention will be fully understood by the following description. Also, benefits of the present invention will be apparent from the following explanation.

DESCRIPTION OF THE EMBODIMENTS

A method for producing a fluoroaryl metal compound to be purified by a purifying method in accordance with the present invention is not especially limited, and various methods can be adopted. A general method is to produce a fluoroaryl metal compound by reacting fluoroaryl magnesium halide (a Grignard reagent) having a corresponding substituent with an organic metal compound having a corresponding metal (such as dimethyltin dichloride), in a solvent containing an ether solvent. In a reaction solution obtained by this method, that is, in a solution containing a fluoroaryl metal compound, which is an object, and the ether solvent, magnesium halide, which is a by-product, is contained in a state that it is dissolved or partly suspended. Here, it is possible to remove the magnesium halide contained in a suspended state by filtration. However, most of (or all of) magnesium halide is dissolved in the solution containing the ether solvent, and thus, in order to obtain a highly pure fluoroaryl metal compound, it is necessary to remove the magnesium halide dissolved in the solution.

The method for purifying a fluoroaryl metal compound in accordance with the present invention is a method for precipitating and removing magnesium halide from a solution containing the fluoroaryl metal compound, the magnesium halide, and an ether solvent. Besides, the method for purifying a fluoroaryl metal compound in accordance with the present invention is a method for removing magnesium halide from a solution containing the fluoroaryl metal compound, the magnesium halide, and an ether solvent, by treating the solution with an acid.

The fluoroaryl metal compound to be purified by the purifying method in accordance with the present invention is a compound represented by General Formula (1):

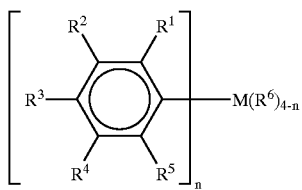

(1)

where each of $R^1$, $R^2$, $R^3$, $R^4$, and $R^5$ independently represents a hydrogen atom, a fluorine atom, a hydrocarbon group, or an alkoxy group, provided that at least one of $R^1$–$R^5$ represents a fluorine atom, M represents a metal atom which belongs to the group IV, $R^6$ represents a hydrocarbon group, and n represents one of 1 through 3. Examples of the hydrocarbon group in substituents denoted as $R^1$ through $R^5$ in the formula specifically include: an aryl group such as a phenyl group; a straight-chain, or branched-chain alkyl group having 1 through 12 carbon atoms, or a cyclic alkyl group having 3 through 12 carbon atoms; and a straight-chain, or branched-chain alkenyl group having 2 through 12 carbon atoms, or a cyclic alkenyl group having 3 through 12 carbon atoms. Examples of the alkyl group specifically include a methyl group, an ethyl group, a propyl group, an isopropyl group, a butyl group, an isobutyl group, a t-butyl group, a pentyl group, an isopentyl group, a t-pentyl group, a hexyl group, an octyl group, a cyclopropyl group, a cyclobutyl group, a cyclopentyl group, and a cyclohexyl group. Examples of the alkenyl group specifically include an allyl group. Incidentally, the hydrocarbon group may further include a functional group including an atom inert to the purifying method (treatment method) in accordance with the present invention, for example, a fluorine atom, a nitrogen atom, an oxygen atom, a sulfur atom, etc., that is, an inert functional group. Examples of the functional group specifically include a methoxy group, a methylthio group, an N,N-dimethylamino group, an o-anise group, a p-anise group, a trimethylsilyloxy group, a dimethyl-t-butylsilyloxy group, and a trifluoromethyl group.

In the formula, the alkoxy group in the substituents denoted as $R^1$ through $R^5$ is represented by General Formula (A):

$$-OR_a \qquad (A)$$

where $R_a$ represents a hydrocarbon group. Examples of the hydrocarbon group denoted as $R_a$ in the formula specifically include: an aryl group such as a phenyl group; a straight-chain, or branched-chain alkyl group having 1 through 12 carbon atoms, or a cyclic alkyl group having 3 through 12 carbon atoms; and a straight-chain, or branched-chain alkenyl group having 2 through 12 carbon atoms, or a cyclic alkenyl group having 3 through 12 carbon atoms. The hydrocarbon group may further include a functional group inert to the purifying method in accordance with the present invention. Examples of the alkoxy group represented by General Formula (A) specifically include a methoxy group, an ethoxy group, an n-propoxy group, an isopropoxy group, an n-butoxy group, an isobutoxy group, a sec-butoxy group, a t-butoxy group, a cyclohexyloxy group, an allyloxy group, and a phenoxy group.

Examples of the hydrocarbon group denoted as $R^6$ in the formula specifically include substituents as in the case of the hydrocarbon group denoted as $R^1$ through $R^5$. Of the substituents, a methyl group, an ethyl group, a propyl group, an isopropyl group, a butyl group, an isobutyl group, and a t-butyl group are more preferable. Tin is particularly preferable as a metal atom which belongs to the group IV (in short periodic type: the groups 4 and 14 in long periodic type) denoted as M in the formula.

Therefore, examples of the fluoroaryl metal compound specifically include p-fluorophenyltrimethyltin, 2,6-difluorophenyltrimethyltin, 2,4,6-trifluorophenyltrimethyltin, 2,3,5,6-tetrafluorophenyltrimethyltin, pentafluorophenyltrimethyltin, p-fluorophenyltributyltin, 2,6-difluorophenyltributyltin, 2,4,6-trifluorophenyltributyltin, 2,3,5,6-tetrafluorophenyltributyltin, pentafluorophenyltributyltin, bis(p-fluorophenyl)-dimethyltin, bis(2,6-difluorophenyl)dimethyltin, bis(2,4,6-trifluorophenyl)dimethyltin, bis(2,3,5,6-tetrafluorophenyl)dimethyltin, bis(pentafluorophenyl)-dimethyltin, bis(p-fluorophenyl)dibutyltin, bis(2,6-difluorophenyl)dibutyltin, bis(2,4,6-trifluorophenyl)-dibutyltin, bis(2,3,5,6-tetrafluorophenyl)dibutyltin, bis(pentafluorophenyl)dibutyltin, tris(p-fluorophenyl)-methyltin, tris(2,6-difluorophenyl)methyltin, tris(2,4,6-trifluorophenyl)dmethyltin, tris(2,3,5,6-tetrafluorophenyl)dmethyltin, tris(pentafluorophenyl)-methyltin, tris(p-fluorophenyl)butyltin, tris(2,6-difluorophenyl)butyltin, tris(2,4,6-trifluorophenyl)-butyltin, tris(2,3,5,6-tetrafluorophenyl)butyltin, and tris(pentafluorophenyl)butyltin.

The magnesium halide to be purified by the purifying method in accordance with the present invention is a compound represented by General Formula (2):

$$MgX_aX_b \qquad (2)$$

where $X_a$ represents a fluorine atom, a chlorine atom, a bromine atom, or an iodine atom, and $X_b$ represents a chlorine atom, a bromine atom, or an iodine atom. Therefore, specifically, the magnesium halide is at least one compound selected from the group consisting of magnesium fluoride chloride, magnesium fluoride bromide, magnesium fluoride iodide, magnesium dichloride, magnesium chloride bromide, magnesium chloride iodide, magnesium dibromide, magnesium bromide iodide, and magnesium diiodide. Besides, the purifying method of the present invention can be applied also to a reaction system in which these compounds are mixed.

Examples of the ether solvent contained in the solution containing the fluoroaryl metal compound and the magnesium halide in accordance with the present invention specifically include: chain ether solvents such as dimethyl ether, diethyl ether, dipropyl ether, diisopropyl ether, dibutyl ether, diisobutyl ether, di-t-butyl ether, dipentyl ether, dihexyl ether, dioctyl ether, t-butylmethyl ether, dimethoxy methane, diethoxy methane, 1,2-dimethoxy ethane, 1,2-diethoxy ethane, etc.; cyclic ether solvents including tetrahydrofuran, tetrahydropyran, 1,4-dioxane, and 1,3-dioxolane; and aromatic ether solvents such as anisole and phenetole, etc. A kind of or a mixture of two or more kinds of ether solvents selected from these example ether solvents can be used effectively. Of all these example ether solvents, diethyl ether, dipropyl ether, diisopropyl ether, dibutyl ether, di-t-butyl ether, t-butylmethyl ether, 1,2-dimethoxy ethane, 1,2-diethoxy ethane, tetrahydrofuran, tetrahydropyran, and anisole are more preferable, and diethyl ether, dipropyl ether, diisopropyl ether, and dibutyl ether are especially preferable.

Besides, examples of other solvents which may be used together with the ether solvent specifically include: aliphatic hydrocarbon solvents such as pentane, hexane, heptane, and octane, etc.; alicyclic hydrocarbon solvents such as cyclopentane, cyclohexane, cycloheptane, and methylcyclohexane, etc.; and aromatic hydrocarbon solvents such as benzene, toluene, and xylene, etc. Such other solvents can be used as long as they are the compounds which do not inhibit with the purifying method in accordance with the present invention.

Further, the ether solvent (and other solvents which may be used together with the ether solvent) contained in the solution in accordance with the present invention may be the ether solvent used when preparing the fluoroaryl magnesium halide by reacting fluoroaryl halide with magnesium, or may be the ether solvent used when producing the fluoroaryl metal compound by reacting the fluoroaryl magnesium halide with the organic metal compound. Specifically, as the ether solvents, the foregoing ether solvents can be named. Of all these ether solvents, diethyl ether, dipropyl ether, diisopropyl ether, dibutyl ether, di-t-butyl ether, t-butylmethyl ether, 1,2-dimethoxy ethane, 1,2-diethoxy ethane, tetrahydrofuran, tetrahydropyran, and anisole are more preferable, and diethyl ether, dipropyl ether, diisopropyl ether, and dibutyl ether are especially preferable.

As for the concentration of the fluoroaryl metal compound in the solution in accordance with the present invention, in order to carry out purifying effectively, it is more preferable that the maximum value is less than the saturated concentration, and that the minimum value is more than 0.1 wt %, further preferably, more than 1 wt %. The concentration of the magnesium halide in the solution in accordance with the present invention is, more preferably, within the range of 0.1 wt % to 80 wt %, further preferably, within the range of 1 wt % to 50 wt %. The molar ratio between the fluoroaryl metal compound and the magnesium halide in the solution is more preferably within the range of 1000:1 to 1:1000, further preferably, within the range of 100:1 to 1:100.

In the purifying method in accordance with the present invention, examples of the method for precipitating/depositing the magnesium halide as solid and removing the magnesium halide from the solution containing the fluoroaryl metal compound, the magnesium halide, and the ether solvent (hereinafter simply referred to as the solution in some cases) specifically include: (1) a method in which the foregoing solution is mixed with a solvent which does not dissolve the magnesium halide (hereinafter referred to as a solvent A); (2) a method in which a residue (a concentrated solution) obtained by distilling out the ether solvent from the foregoing solution and the solvent A are mixed; (3) a method in which the foregoing solution is mixed with a solvent which has a boiling point higher than that of the ether solvent contained in the foregoing solution and which does not dissolve the magnesium halide (hereinafter referred to as a solvent B), then the ether solvent is distilled out from the mixed solution, and the concentrated solution is cooled as necessary; (4) a method in which the solvent B is heated to a temperature higher than the boiling point of the ether solvent contained in the foregoing solution, then the ether solvent is distilled out with the foregoing solution being added to the solvent B, and the concentrated solution is cooled as necessary, etc.

Examples of the solvents A and B specifically include: aliphatic hydrocarbon solvents such as pentane, hexane, heptane, and octane, etc.; alicyclic hydrocarbon solvents such as cyclopentane, cyclohexane, cycloheptane, and methylcyclohexane, etc.; aromatic hydrocarbon solvents such as benzene, toluene, and xylene, etc.; and ether solvents such as diisopropyl ether, and dibutyl ether, etc. A kind or a mixture of two or more kinds selected from these example solvents can be used as the solvent A or B. The amount of the solvent A or B used with respect to the solution is satisfactorily specified as long as they are sufficient to carry out purifying effectively. When two or more kinds of the solvents are used so as to constitute the solvent A or B, the ratio of the respective solvents in the solvent A or B can be specified conveniently. Besides, mixed hydrocarbon solvents such as IsoparC, IsoparE, and IsoparG (all of them are trademarks), which are commercially available hydrocarbon solvents manufactured by Exxon Corporation, can be used as the solvent A or B.

As for the method for mixing the solution and the solvent A in the foregoing methods (1) and (2), the solvent A may be added to the solution, or the solution may be added to the solvent A. Specifically, the temperature when mixing the solution and the solvent A is, more preferably, within the range of −100° C. to 2000° C., further preferably, within the range of −50° C. to 150° C., and most preferably, within the range of −200° C. to 120° C.

As for the method for mixing the solution and the solvent B in the foregoing method (3), the solvent B may be added to the solution, or the solution may be added to the solvent B. Specifically, the temperature when mixing the solution and the solvent B is, more preferably, within the range of −100° C. to 200° C., further preferably, within the range of −50° C. to 150° C.

As for the method for distilling out the ether solvent in the foregoing methods (2) to (4), specifically, a method for heating the solution or the mixed solution under a normal pressure (atmospheric pressure) can be adopted. However, a method for heating the solution or the mixed solution under a reduced or increased pressure may also be adopted. When the ether solvent is distilled out under a normal pressure, the heating temperature is satisfactorily specified as long as it is more than the boiling point of the ether solvent. Further, the cooling temperature when cooling the concentrated solution obtained by distilling out the ether solvent in the foregoing methods (3) and (4) is satisfactorily specified so that the magnesium halide is sufficiently precipitated.

The magnesium halide can be precipitated/deposited as solid by carrying out the foregoing methods (1) to (4), etc. The magnesium halide can be separated and removed by filtering the solution (concentrated solution) containing the fluoroaryl metal compound and the solvent A or B. In this manner, the fluoroaryl metal compound can be purified easily and inexpensively. That is, a highly-pure fluoroaryl metal compound without having impurities can be obtained easily and inexpensively.

In the purifying method in accordance with the present invention, examples of the method for treating the solution containing the fluoroaryl metal compound, the magnesium halide, and the ether solvent with an acid specifically include: (5) a method in which the foregoing solution and an aqueous solution containing an acid are mixed and stirred, then the mixed solution is allowed to stand so as to be separated into an organic layer containing the fluoroaryl metal compound and an aqueous layer containing the magnesium halide and the acid, and the aqueous layer is removed. The magnesium halide is dissolved in the aqueous solution containing the acid, but the fluoroaryl metal compound is insoluble into the aqueous solution.

As the foregoing acid, inorganic acids and/or organic acids can be used. Examples of the acid specifically include: inorganic acids such as hydrochloric acid, sulfuric acid, nitric acid, phosphoric acid, and carbonic acid, etc.; and organic acids such as formic acid, acetic acid, propionic acid, oxalic acid, malonic acid, and succinic acid, etc. A kind or a mixture of two or more kinds, such as a mixture of an inorganic acid and an organic acid, selected from these example acids can be used. As for the acid which can be used in the present invention, at least one kind of acid selected from the group consisting of hydrochloric acid, sulfuric acid, nitric acid, phosphoric acid, carbonic acid, formic acid, acetic acid, propionic acid, oxalic acid, malonic acid, and succinic acid is preferable. Of these example acids, at least one kind of acid selected from the group consisting of hydrochloric acid, sulfuric acid, nitric acid, phosphoric acid, formic acid, acetic acid, oxalic acid, malonic acid, and succinic acid is more preferable. It is preferable that the amount of the acid to be used is more than 0.01 equivalent, more preferably, more than 0.1 equivalent, with respect to the magnesium halide contained in the solution, so as to efficiently carry out purifying. The concentration of the acid in the aqueous solution and the method for preparing the aqueous solution containing the acid can be specified conveniently. When two or more kinds of the acids are used, the ratio of the respective acids can be specified conveniently.

As for the method for mixing the solution with the aqueous solution containing the acid in the foregoing method (5), the aqueous solution may be added to the solution, or the solution may be added to the aqueous solution. It is preferable that the temperature when mixing and stirring the solution and the aqueous solution containing the acid is higher than the temperature at which the fluoroaryl metal compound is precipitated out of the solution, and less than the temperature at which the fluoroaryl metal compound is decomposed. Specifically, the range of −100° C. to 200° C. is preferable, the range of −50° C. to 150° C. is more preferable, and the range of −20° C. to 100° C. is further preferable. The period of time when mixing the solution and the aqueous solution containing the acid can be specified conveniently.

The organic layer and the aqueous layer can be separated by a simple procedure such as liquid separating (oil water separating) procedure, but the method for separating the organic layer and the aqueous layer and the method for removing the aqueous layer, that is, the method for removing the magnesium halide and the acid, is not limited to the foregoing method (5). When the acid is contained in the organic layer, it is satisfactory to carry out a simple procedure, for example, washing the organic layer with water, an aqueous solution of sodium carbonate, an aqueous solution of sodium hydrogen carbonate, or an aqueous solution of sodium hydroxide, etc., as necessary. When the fluoroaryl metal compound is contained in the aqueous layer, it is satisfactory to carry out a simple procedure, for example, extracting (recovery) the fluoroaryl metal compound from the aqueous layer using an appropriate solvent, as necessary. Further, when water is contained in the organic layer, it is satisfactory to remove (dry) the water by adding a desiccating agent such as magnesium sulfate, anhydrous to the organic layer, as necessary. Incidentally, the method for treating the solution with the acid, such as the foregoing method (5), may be carried out repeatedly as necessary, so that the magnesium halide contained in the solution is sufficiently removed.

By carrying out the foregoing method (5) or the like, the magnesium halide can be separated and removed. Thus, the fluoroaryl metal compound can be purified easily and inexpensively. That is, a highly pure fluoroaryl metal compound having no impurities can be obtained easily and inexpensively.

As has been discussed, according to the purifying method in accordance with the present invention, the magnesium halide can be separated and removed by a simple procedure (process), and thus the fluoroaryl metal compound can be purified easily and inexpensively. Consequently, according to the purifying method in accordance with the present invention, a highly pure fluoroaryl metal compound having no impurities can be obtained easily and inexpensively.

Besides, in carrying out the purifying method of the present invention, the Grignard exchange reaction can be named as a method for obtaining a more preferable fluoroaryl metal compound. By combining the purifying method of the present invention and the Grignard exchange reaction, by-products are less produced, and purifying process can be simplified, therefore a reaction path preferable as an industrial embodiment can be obtained.

In the following, the present invention will be explained in detail by way of examples, but the present invention is not limited to the disclosure below. Incidentally, the $^{19}$F-NMR (Nuclear Magnetic Resonance) spectrum data in the examples was measured using trifluoroacetic acid as a reference material. The signal of the reference material was set at 0 ppm.

Example 1

First, a solution containing a fluoroaryl metal compound, magnesium halide, and an ether solvent was produced. That is, 9.73 g (0.400 mol) of magnesium was charged to a first reaction vessel equipped with a reflux condenser, a thermometer, a dropping funnel, a nitrogen gas conduit, and a stirrer, and air inside the first reaction vessel was satisfactorily displaced by a nitrogen gas. Next, 300 ml of diethyl ether as an ether solvent was charged to the first reaction vessel, and 90.00 g (0.364 mol) of bromopentafluorobenzene as fluoroaryl halide was charged to the dropping funnel. Then, the bromopentafluorobenzene was dropped from the dropping funnel over two hours, with stirring the content of the first reaction vessel and keeping the inside temperature at a reflux temperature of diethyl ether (35° C.) under a nitrogen gas atmosphere. When the dropping was completed, the content was further stirred at the same temperature for three hours and maturated. Consequently, a diethyl ether solution of pentafluorophenyl magnesium bromide, which is fluoroaryl magnesium halide, was obtained.

Then, 38.60 g (0.176 mol) of dimethyltin dichloride as an organic metal compound was charged to a second reaction vessel, which is similar to the first reaction vessel, and air inside the second reaction vessel was satisfactorily displaced by a nitrogen gas. Next, 100 ml of diethyl ether was charged to the second reaction vessel, and the diethyl ether solution of the pentafluorophenyl magnesium bromide was charged to the dropping funnel. Then, the diethyl ether solution was dropped from the dropping funnel over two hours, with stirring the content of the second reaction vessel and keeping the inside temperature at the reflux temperature of diethyl ether under a nitrogen gas atmosphere. When the dropping was completed, the content was further stirred at the same temperature for one hour.

In such a manner, a solution containing bis(pentafluorophenyl)dimethyltin as a fluoroaryl metal compound, magnesium chloride bromide as magnesium halide, and diethyl ether was obtained. The reaction yield was analyzed by a $^{19}$F-NMR. That is, $^{19}$F-NMR was measured under predetermined conditions, using p-fluorotoluene as an internal reference. Then, an integral value of a fluorine atom of the p-fluorotoluene and an integral value of a fluorine atom of an ortho position of a pentafluorophenyl group of the bis(pentafluorophenyl)dimethyltin were given from the obtained $^{19}$F-NMR chart, and the amount of the bis(pentafluorophenyl)dimethyltin was calculated from these two integral values. As a result, 80.38 g (0.166 mol) of bis(pentafluorophenyl)dimethyltin was contained in the solution.

Next, the purifying method in accordance with the present invention was carried out using the solution produced by the foregoing method. That is, 200 ml of IsoparE (a hydrocarbon solvent manufactured by Exxon Corporation) as the solvent B was charged to a reaction vessel equipped with a condenser, a thermometer, a dropping funnel, and a stirrer, and the foregoing solution was charged to the dropping funnel. Then, the content of the reaction vessel was heated to 100° C. with being stirred, and the solution was dropped from the dropping funnel over one hour with distilling out diethyl ether. The inside temperature of the reaction vessel while the solution was dropped was kept at 90° C. to 100° C. When the dropping was completed, the content of the reaction vessel was heated to 116° C., so as to completely distill out diethyl ether.

Next, the content of the reaction vessel (a concentrated solution) was cooled to 30° C., and the resultant precipitates (magnesium chloride bromide) were filtered off. In this manner, a solution of bis(pentafluorophenyl)dimethyltin in IsoparE was obtained. The solution was colored in amber. As a result of analysis by a $^{19}$F-NMR, 78.41 g (0.162 mol) of bis(pentafluorophenyl)dimethyltin was contained in the solution, and its purity was 98.7%, and its yield was 91.1%, based on dimethyltin dichloride. As a result of analysis by a fluorescent X-ray, the solution did not contain magnesium chloride bromide.

Example 2

First, a solution containing 80.38 g (0.166 mol) of bis(pentafluorophenyl)dimethyltin, magnesium chloride bromide, and diethyl ether was obtained by a method similar to that in Example 1.

Here, 400 g of an aqueous solution of 1M-hydrochloric acid as an aqueous solution containing an acid was charged to a reaction vessel which is equipped with a reflux condenser, a thermometer, a dropping funnel, a nitrogen gas conduit, and a stirrer, and has a drain cock on its bottom, and air inside the reaction vessel was satisfactorily displaced by a nitrogen gas. Next, the foregoing solution was charged to the dropping funnel. Then, the foregoing solution was dropped from the dropping funnel over 30 minutes, with stirring the content of the reaction vessel under a nitrogen gas atmosphere. The inside temperature of the reaction vessel while the foregoing solution was dropped was kept at 25° C. to 40° C. When the dropping was completed, the content (the mixed solution) of the reaction vessel was allowed to stand so as to be separated into an organic layer and an aqueous layer, and the aqueous layer was removed via the drain cock.

Next, 200 g of a saturated aqueous solution of sodium carbonate was charged to the reaction vessel, and the content was stirred and mixed for 30 minutes. Then, the mixed solution was allowed to stand so as to be separated into an organic layer and an aqueous layer, and the aqueous layer was removed via the drain cock. Further, 100 g of saturated aqueous solution of sodium chloride was charged to the reaction vessel, and the content was stirred and mixed for 30 minutes. Then, the mixed solution was allowed to stand so as to be separated into an organic layer and an aqueous layer, and the aqueous layer was removed via the drain cock. Next, the organic layer was taken out and dried over magnesium sulfate, anhydrous, then the magnesium sulfate, anhydrous was filtered off. In this manner, a diethyl ether solution containing bis(pentafluorophenyl)dimethyltin was obtained.

By distilling out diethyl ether from the foregoing diethyl ether solution, 80.50 g of a black liquid containing bis(pentafluorophenyl)dimethyltin was obtained. As a result of analysis by a $^{19}$F-NMR, 79.53 g (0.164 mol) of bis(pentafluorophenyl)dimethyltin was contained in the liquid, and its purity was 98.8%, and its yield was 93.6%, based on dimethyltin dichloride. As a result of analysis by a fluorescent X-ray, the solution did not contain magnesium chloride bromide.

Example 3

First, a solution containing 80.38 g (0.166 mol) of bis(pentafluorophenyl)dimethyltin, magnesium chloride bromide, and diethyl ether was obtained by a method similar to that in Example 1.

The foregoing solution was charged to a reaction vessel which is equipped with a reflux condenser, a thermometer, a dropping funnel, a nitrogen gas conduit, and a stirrer, and has a drain cock on its bottom, and air inside the reaction vessel was satisfactorily displaced by a nitrogen gas. Next, 400 g of an aqueous solution containing 20.94 g of acetic acid as an aqueous solution containing an acid was charged to the dropping funnel. Then, the foregoing aqueous solution was dropped from the dropping funnel over 30 minutes, with stirring the content of the reaction vessel under a nitrogen gas atmosphere. The inside temperature of the reaction vessel while the foregoing aqueous solution was dropped was kept at 25° C. to 40° C. When the dropping was completed, the content (the mixed solution) of the reaction vessel was allowed to stand so as to be separated into an organic layer and an aqueous layer, and the aqueous layer was removed via the drain cock.

Next, 200 g of a saturated aqueous solution of sodium carbonate was charged to the reaction vessel, and the content was stirred and mixed for 30 minutes. Then, the mixed solution was allowed to stand so as to be separated into an organic layer and an aqueous layer, and the aqueous layer was removed via the drain cock.

Further, 100 g of saturated aqueous solution of sodium chloride was charged to the reaction vessel, and the content was stirred and mixed for 30 minutes. Then, the mixed solution was allowed to stand so as to be separated into an organic layer and an aqueous layer, and the aqueous layer was removed via the drain cock. Next, the organic layer was taken out and dried over magnesium sulfate, anhydrous, then the magnesium sulfate, anhydrous was filtered off. In this manner, a diethyl ether solution containing bis(pentafluorophenyl)dimethyltin was obtained.

By distilling out diethyl ether from the foregoing diethyl ether solution, 80.38 g of a black liquid containing bis(pentafluorophenyl)dimethyltin was obtained. As a result of analysis by a $^{19}$F-NMR, 79.22 g of bis(pentafluorophenyl)dimethyltin was contained in the liquid, and its purity was 98.7%, and its yield was 93.2%, based on dimethyltin dichloride. As a result of analysis by a fluorescent X-ray, the solution did not contain magnesium chloride bromide.

Example 4

First, a solution containing a fluoroaryl metal compound, magnesium halide, and an ether solvent is produced. That is, 5.00 g (0.206 mol) of magnesium was charged to a first reaction vessel similar to that in Example 1, and air inside the reaction vessel was satisfactorily displaced by a nitrogen gas. Next, 150 ml of dibutyl ether was charged to the first reaction vessel, and 21.22 g (0.195 mol) of ethyl bromide was charged to a dropping funnel. Then, the ethyl bromide was dropped from the dropping funnel over 30 minutes, with stirring the content of the first reaction vessel and keeping the inside temperature of the first reaction vessel at 30° C. to 40° C. under a nitrogen gas atmosphere. When the dropping was completed, the content was further stirred at the same temperature for two hours and maturated. On the other hand, 45.0 g (0.182 mol) of bromopentafluorobenzene was charged to the dropping funnel.

Next, the bromopentafluorobenzene was dropped from the dropping funnel over 30 minutes, with stirring the content of the first reaction vessel and keeping the inside temperature at 30° C. to 40° C. under the nitrogen gas atmosphere. When the dropping was completed, the content was further stirred at the same temperature for two hours and maturated. Consequently, pentafluorophenyl magnesium bromide was obtained as a dibutyl ether solution.

Then, 19.12 g (0.087 mol) of dimethyltin dichloride was charged to a second reaction vessel similar to that in Example 1, and air inside the second reaction vessel was satisfactorily displaced by a nitrogen gas. Next, 100 ml of dibutyl ether as a solvent was charged to the second reaction vessel, and the dibutyl ether solution of the pentafluorophenyl magnesium halide was charged to a dropping funnel. Then, the dibutyl ether solution was dropped from the dropping funnel over two hours, with stirring the content of the second reaction vessel and keeping the inside temperature at 30° C. to 40° C. under a nitrogen gas atmosphere. When the dropping was completed, the content was further stirred at the same temperature for one hour.

Consequently, a dibutyl ether solution containing bis(pentafluorophenyl)dimethyltin as a fluoroaryl metal compound and magnesium chloride bromide as a magnesium halide was obtained.

Next, 250 g of an aqueous solution of 1M-hydrochloric acid was charged to the dropping funnel, as an aqueous solution containing an acid. Then, the aqueous solution in the dropping funnel was dropped over one hour, with stirring the content of the foregoing reaction vessel and keeping the inside temperature at less than 400° C. When the dropping was completed, the content of the reaction vessel was moved to a separating funnel and allowed to stand so as to be separated into an organic layer and an aqueous layer, and the aqueous layer was drained. Consequently, bis(pentafluorophenyl)-dimethyltin as a fluoroaryl metal compound was obtained as a dibutyl ether solution. As a result of analysis by a method identical to that used in Example 1, the purity was 98.8%, and the yield was 95.3%, based on dimethyltin dichloride. As a result of analysis by a fluorescent X-ray, the solution did not contain magnesium chloride bromide.

Example 5

First, a solution containing a fluoroaryl metal compound, magnesium halide, and an ether solvent is produced. That is, 3.23 g (0.133 mol) of magnesium was charged to a first reaction vessel similar to that in Example 1, and air inside the reaction vessel was satisfactorily displaced by a nitrogen gas. Next, 150 ml of diisopropyl ether was charged to the first reaction vessel, and 13.43 g (0.123 mol) of ethyl bromide was charged to a dropping funnel. Then, the ethyl bromide was dropped from the dropping funnel over two hours, with stirring the content of the first reaction vessel and keeping the inside temperature of the first reaction vessel at 30° C. to 40° C. under a nitrogen gas atmosphere. When the dropping was completed, the content was further stirred at the same temperature for 30 minutes and maturated. On the other hand, 29.99 g (0.121 mol) of bromopentafluorobenzene was charged to the dropping funnel.

Next, the bromopentafluorobenzene was dropped from the dropping funnel over two hours, with stirring the content of the first reaction vessel and keeping the inside temperature at 30° C. to 40° C. under the nitrogen gas atmosphere. When the dropping was completed, the content was further stirred at the same temperature for 30 minutes and maturated. Consequently, pentafluorophenyl magnesium bromide was obtained as a diisopropyl ether solution.

Then, 17.54 g (0.058 mol) of dibutyltin dichloride was charged to the reaction vessel, and the content was stirred at room temperature for three hours. Consequently, a diisopropyl ether suspension containing bis(pentafluorophenyl)dibutyltin as a fluoroaryl metal compound and magnesium chloride bromide as a magnesium halide was obtained.

After the reaction was completed, the resultant precipitates (magnesium chloride bromide) were filtered off. Next, 100 ml of hexane was added to the residue obtained by concentrating the filtrate so as to precipitate impurities contained in the residue, then the resultant precipitates were filtered off. Consequently, bis(pentafluorophenyl)dibutyltin as a fluoroaryl metal compound was obtained as a hexane solution. As a result of analysis by a method identical to that used in Example 1, the purity was 99.2%, and the yield was 95.4%, based on dibutyltin dichloride. As a result of analysis by a fluorescent X-ray, the solution did not contain magnesium chloride bromide.

As has been discussed, a method for purifying a fluoroaryl metal compound of the present invention is structured so as to precipitate and remove magnesium halide from a solution containing the fluoroaryl metal compound, the magnesium halide, and an ether solvent.

The method for purifying a fluoroaryl metal compound of the present invention is structured so as to remove magnesium halide from a solution containing the fluoroaryl metal compound, the magnesium halide, and an ether solvent, by treating the solution with an acid.

The method for purifying a fluoroaryl metal compound of the present invention is structured so that a metal atom contained in the fluoroaryl metal compound is tin. The method for purifying a fluoroaryl metal compound of the present invention is further structured so that the fluoroaryl metal compound is bis(pentafluorophenyl)dialkyltin.

Therefore, the magnesium halide can be separated and removed by a simple procedure (process), and thus the fluoroaryl metal compound can be purified easily and inexpensively. That is, the method of the present invention has an effect to easily and inexpensively obtain a highly pure fluoroaryl metal compound containing no impurities.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for purifying a fluoroaryl metal compound represented by General Formula (1):

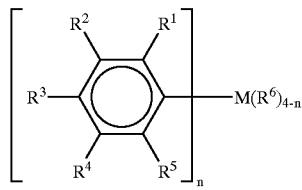
(1)

where each of $R^1$, $R^2$, $R^3$, $R^4$, and $R^5$ independently represents one of a hydrogen atom, a fluorine atom, a hydrocarbon group, and an alkoxy group, provided that at least one of $R^1$–$R^5$ represents a fluorine atom, M represents a metal atom which belongs to the group IV, $R^6$ represents a hydrocarbon group, and n represents one of 1 through 3, comprising the step of precipitating and removing magnesium halide represented by General Formula (2):

$$MgX_aX_b \qquad (2)$$

where $X_a$ represents one of a fluorine atom, a chlorine atom, a bromine atom, and an iodine atom, and $X_b$ represents one of a chlorine atom, a bromine atom, and an iodine atom, from a solution containing said fluoroaryl metal compound, said magnesium halide, and an ether solvent.

2. The method for purifying a fluoroaryl metal compound of claim 1, wherein:
said solution is mixed with a solvent A which does not dissolve said magnesium halide.

3. The method for purifying a fluoroaryl metal compound of claim 1, wherein:
a residue obtained by distilling out said ether solvent from said solution is mixed with a solvent A which does not dissolve said magnesium halide.

4. The method for purifying a fluoroaryl metal compound of claim 1, wherein:
said solution is mixed with a solvent B which has a boiling point higher than that of said ether solvent and which does not dissolve said magnesium halide, then said ether solvent is distilled out from a mixed solution, and a concentrated solution is cooled as necessary.

5. The method for purifying a fluoroaryl metal compound of claim 1, wherein:
a solvent B which has a boiling point higher than that of said ether solvent contained in said solution and which does not dissolve said magnesium halide is heated to a temperature higher than a boiling point of said ether solvent contained in said solution, then said ether solvent is distilled out with said solution being added to said solvent B, and a concentrated solution is cooled as necessary.

6. A method for purifying a fluoroaryl metal compound represented by General Formula (1):

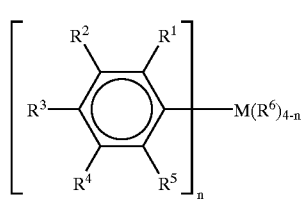
(1)

where each of $R^1$, $R^2$, $R^3$, $R^4$, and $R^5$ independently represents one of a hydrogen atom, a fluorine atom, a hydrocarbon group, and an alkoxy group, provided that at least one of $R^1$–$R^5$ represents a fluorine atom, M represents a metal atom which belongs to the group IV, $R^6$ represents a hydrocarbon group, and n represents one of 1 through 3, comprising the step of removing magnesium halide represented by General Formula (2):

$$MgX_aX_b \qquad (2)$$

where $X_a$ represents one of a fluorine atom, a chlorine atom, a bromine atom, and an iodine atom, and $X_b$ represents one of a chlorine atom, a bromine atom, and an iodine atom, from a solution containing said fluoroaryl metal compound, said magnesium halide, and an ether solvent, by treating said solution with an acid.

7. The method for purifying a fluoroaryl metal compound of claim 6, wherein:
said solution and an aqueous solution containing said acid are mixed and stirred, and a mixed solution is allowed to stand so as to be separated into an organic layer containing said fluoroaryl metal compound and an aqueous layer containing said magnesium halide and said acid, and said aqueous layer is removed.

8. The method for purifying a fluoroaryl metal compound of claim 6, wherein:
said acid is at least one kind of acid selected from the group consisting of an inorganic acid and an organic acid.

9. The method for purifying a fluoroaryl metal compound of claim 6, wherein:
said acid is at least one kind of acid selected from the group consisting of hydrochloric acid, sulfuric acid, nitric acid, phosphoric acid, carbonic acid, formic acid, acetic acid, propionic acid, oxalic acid, malonic acid, and succinic acid.

10. The method for purifying a fluoroaryl metal compound of claim 1, wherein:
a molar ratio of said fluoroaryl metal compound and said magnesium halide in said solution is within a range of 1000:1 to 1:1000.

11. The method for purifying a fluoroaryl metal compound of claim 6, wherein:

a molar ratio of said fluoroaryl metal compound and said magnesium halide in said solution is within a range of 1000:1 to 1:1000.

12. The method for purifying a fluoroaryl metal compound of claim 1, wherein:
the metal atom contained in said fluoroaryl metal compound is tin.

13. The method for purifying a fluoroaryl metal compound of claim 6, wherein:
the metal atom contained in said fluoroaryl metal compound is tin.

14. The method for purifying a fluoroaryl metal compound of claim 1, wherein:
said fluoroaryl metal compound is bis(pentafluoroaryl) dialkyltin.

15. The method for purifying a fluoroaryl metal compound of claim 6, wherein:
said fluoroaryl metal compound is bis(pentafluoroaryl) dialkyltin.

16. The method for purifying a fluoroaryl metal compound of claim 1, wherein:
said magnesium halide is at least one compound selected from the group consisting of magnesium fluoride chloride, magnesium fluoride bromide, magnesium fluoride iodide, magnesium dichloride, magnesium chloride bromide, magnesium chloride iodide, magnesium dibromide, magnesium bromide iodide, and magnesium diiodide.

17. The method for purifying a fluoroaryl metal compound of claim 6, wherein:
said magnesium halide is at least one compound selected from the group consisting of magnesium fluoride chloride, magnesium fluoride bromide, magnesium fluoride iodide, magnesium dichloride, magnesium chloride bromide, magnesium chloride iodide, magnesium dibromide, magnesium bromide iodide, and magnesium diiodide.

18. The method for purifying a fluoroaryl metal compound of claim 1, wherein:
said ether solvent is at least one solvent selected from the group consisting of diethyl ether, dipropyl ether, diisopropyl ether, dibutyl ether, di-t-butyl ether, t-butylmethyl ether, 1,2-dimethoxy ethane, 1,2-diethoxy ethane, tetrahydrofuran, tetrahydropyran, and anisole.

19. The method for purifying a fluoroaryl metal compound of claim 6, wherein:
said ether solvent is at least one solvent selected from the group consisting of diethyl ether, dipropyl ether, diisopropyl ether, dibutyl ether, di-t-butyl ether, t-butylmethyl ether, 1,2-dimethoxy ethane, 1,2-diethoxy ethane, tetrahydrofuran, tetrahydropyran, and anisole.

20. The method for purifying a fluoroaryl metal compound of claim 2, wherein:
said solvent A is at least one solvent selected from the group consisting of an aliphatic hydrocarbon solvent, an alicyclic hydrocarbon solvent, an aromatic hydrocarbon solvent, and an ether solvent.

21. The method for purifying a fluoroaryl metal compound of claim 3, wherein:
said solvent A is at least one solvent selected from the group consisting of an aliphatic hydrocarbon solvent, an alicyclic hydrocarbon solvent, an aromatic hydrocarbon solvent, and an ether solvent.

22. The method for purifying a fluoroaryl metal compound of claim 4, wherein:
said solvent B is at least one solvent selected from the group consisting of an aliphatic hydrocarbon solvent, an alicyclic hydrocarbon solvent, an aromatic hydrocarbon solvent, and an ether solvent.

23. The method for purifying a fluoroaryl metal compound of claim 5, wherein:
said solvent B is at least one solvent selected from the group consisting of an aliphatic hydrocarbon solvent, an alicyclic hydrocarbon solvent, an aromatic hydrocarbon solvent, and an ether solvent.

* * * * *